(12) United States Patent
Yong

(10) Patent No.: US 6,497,728 B2
(45) Date of Patent: Dec. 24, 2002

(54) METAL JACKET FOR A CEMENTLESS ARTIFICIAL JOINT STEM AND ARTIFICIAL JOINT HAVING THE JACKET

(75) Inventor: Yoon San Yong, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/777,704

(22) Filed: Feb. 7, 2001

(65) Prior Publication Data

US 2001/0016780 A1 Aug. 23, 2001

(30) Foreign Application Priority Data

Feb. 16, 2000 (KR) .......................................... 2000-7363

(51) Int. Cl.[7] .................................................. A61F 2/36
(52) U.S. Cl. ................................ 623/23.46; 623/23.52; 623/23.22
(58) Field of Search ........................... 623/23.21, 23.22, 623/23.23, 23.25, 23.46, 23.48, 23.52

(56) References Cited

U.S. PATENT DOCUMENTS

| | | | | |
|---|---|---|---|---|
| 4,064,567 A | * | 12/1977 | Burstein | 623/23.46 |
| 4,728,335 A | * | 3/1988 | Jurgutis | 623/23.46 |
| 4,790,852 A | * | 12/1988 | Noiles | 623/23.46 |
| 4,846,839 A | * | 7/1989 | Noiles | 623/23.46 |
| 4,936,859 A | * | 6/1990 | Morscher | 623/23.46 |
| 5,057,101 A | * | 10/1991 | Dorr | 623/23.46 |
| 5,976,188 A | * | 11/1999 | Dextradeur | 623/23.46 |
| 6,139,584 A | * | 10/2000 | Ochoa | 623/23.46 |
| 6,245,113 B1 | * | 6/2001 | Revie | 623/23.46 |

* cited by examiner

Primary Examiner—Bruce Snow
(74) Attorney, Agent, or Firm—Duane Morris LLP

(57) ABSTRACT

The present invention is intended to provide a metal jacket for a cementless artificial joint stem, wherein shear force detrimental to the service life of an artificial joint can be markedly reduced and stress shielding phenomena can also be markedly relieved, due to the construction of the metal jacket which can be fixed to the bone and can enclose the surface of the stem so as to allow for the stem of artificial joint to slide vertically relative to the bone, and wherein osteolysis of a bone due to the infiltration of wear particles can be minimized by curbing the gap formation between the bone and the stem.

To that end, there is provided according to the invention, a metal jacket for a cementless artificial joint stem, which jacket is so formed as to enclose at least a part of the cementless artificial joint stem 21, said stem with jacket being inserted longitudinally in the opening formed in the bone canal of a human body, and on the surface of which jacket surface-processed metal layer or metal wires 12 is formed so that the bone can make interlocking with the metal jacket as the bone gets on-growth onto the metal jacket.

4 Claims, 4 Drawing Sheets

METAL JACKET FOR A CEMENTLESS ARTIFICIAL JOINT STEM AND ARTIFICIAL JOINT HAVING THE JACKET

BACKGROUND OF THE INVENTION

1. Field of the Invention

The present invention relates to a metal jacket for a cementless artificial joint stem, and particularly to a metal jacket for a cementless artificial joint stem, with said jacket secured to the bone in such a manner that the cementless artificial joint stem can slide relative to the bone and said jacket enclosing the surface of the cementless artificial joint stem. The invention also relates to a cementless artificial joint having the artificial joint stem enclosed in the jacket.

2. Description of the Prior Art

Generally, an artificial hip joint, for example, consists of an acetabular part and a femoral or thigh bone part, wherein the acetabular and femoral parts are made of either metal, plastic, or ceramic, independently.

And the human femur is formed of the soft cancellous bone in the metaphyseal region and hard cortical bone in the diaphyseal region. Therefore, in order to insert an artificial joint into the human body, operation is conducted in such a way that the bone canal is reamed out at the proximal site, the stem of artificial joint is inserted and finally anchorage is conducted by using cement, or in other case of not using cement, a stem having a porous or roughened surface layer on the outer circumference is inserted so as to allow the surface to get physiological interlocking with the bone as it grows.

The art for surgical operation based on the artificial joint using cement out of the two methods as described above is disclosed in the Korean patent publication 1814/1985 to the present applicants as the patentee, titled "Torsion resistant artificial hip joint".

Referring to FIG. 1, the art is briefly reviewed.

The artificial joint 1 is integrally composed of a head 2, neck 3, collar 4 and stem 5, starting with the top. The leading end of the collar 4 is curved to be secured tightly in the inner top edge of the cortex of femur. The stem 5 is in a curved column with the top cross section resembling an ellipse which gradually varies to a circle at the bottom. Such a shape of the stem 5 is intended for protection from rotating due to the compressive force applied vertically from the top of joint and the lateral force applied in perpendicular direction to the stem of joint at the head.

Further, on the upper external surface of such a stem 5 a blade 7 with an appropriate thickness is provided protrusively in longitudinal direction to prevent the joint from turning in the femur even in the case of a torque generated in an arbitrary direction after a surgery, wherein a fixing hole 8 is formed in the center of the blade 7.

On the inward side of the blade 7, the stem 5 is formed with a number of lateral grooves at certain longitudinal intervals, in which grooves iron wires 9 in chain form are inserted in a manner of wrapping the stem. On the surface of the stem 5 including chain-like wires 9, cement 6 is coated to a certain thickness. Such a process of pre-coating with cement 6 is to facilitate adhesion with the cement used in the surgical operation and to reduce the heat generated during curing period through the reduced use of cement.

In order to introduce such an artificial joint in a human long bone, reaming is carried out at the bone canal beforehand so that the artificial joint 1 may be inserted with the stem 5, after appropriate amount of cement is injected thereto. Subsequently, the stem 5 is inserted in the cement-injected area, so that this cement may adhere with the pre-coated cement layer 6 on the surface of the stem 5, with the result that the stem 5 can be firmly secured in the femur.

However, the artificial joint using the cement as described above has the drawback in that the connection is weak due to the fragile cement connection between the joint stem and the bone canal.

In order to compensate for such a drawback, the connection between the femur and the joint stem was modified so as to be physiologically interlocked at the joint stem with the ingrowth or ongrowth of the bone into the porous or rough surface of the stem.

In particular, a joint stem, the surface of which is either made porous or roughened through grit blasting with fine stones, is inserted into the bone canal through a surgical operation. Then, with gradual growth of the bone, the bone physiologically gets interlocked with the porous or roughened surface layer to fix the stem to the femur.

The cementless artificial joint based on a physiological method as described above has the merit over an artificial joint using cement in the respect of strong interface for a biologically active young patient. However, with this cementless artificial joint, there is a risk of impeding the process of the ingrowth of the bone to the joint stem due to the over-sized gap of the bone canal in the magnitude of several millimeters.

In addition, the vertical force applied on the head of the stem may act as the shear force at the interface with the bone to produce a fibrous tissue membrane on the bone, to thereby form an effective joint space. Then the wear particles produced at the plastic cup may penetrate into the gap (effective joint space) formed between the bone and the stem and accelerate osteolysis of the bone as a serious drawback.

Further, for the case of a stem with all of its surface porous, a substantial part of vertical force is transferred to the lower side and thereby the upper side of a femur is associated with the bone resorption from low stress due to stress shielding. And in the case that only the upper part of the stem is made porous, the lower part can produce a micro movement due to the weak connection, resulting in the problem of causing a pain.

Further, in the case of revision surgery because of the trouble with a cementless artificial joint, removal of the stem is very challenging on the ground that the connection between the joint stem and the femur is a physiological one based on the ingrowth of the bone into the porous surface of the metal stem.

SUMMARY OF THE INVENTION

Therefore, the present invention was created to resolve the problem with the conventional art as described above and the object of the present invention is to provide a metal jacket for a cementless artificial joint stem, wherein shear force negative to the service life of an artificial joint can be markedly reduced and stress shielding phenomena can also be markedly relieved, due to the construction of the jacket which can be fixed to the femur and can enclose the surface of the stem so as to allow for the stem of artificial joint to slide vertically relative to the bone canal, and wherein osteolysis of a bone due to the infiltration of wear particles can be minimized by curbing the gap formation between the bone canal and the stem.

Further, another object of the present invention is to provide a cementless artificial joint in which a stem is covered by a metal jacket for a cementless artificial joint stem.

To achieve the above first object, there is provided, according to an aspect of the invention, a metal jacket for the stem of a cementless artificial joint, wherein the jacket is so formed as to enclose at least a part of the stem of a cementless artificial joint, after the jacket is inserted longitudinally in the opening formed in the bone canal of a human body, and wherein on the surface of the metal jacket a surface-roughened metal layer is formed so that the bone can make interlocking with the metal jacket as the bone gets on-growth.

Preferably, the metal layer is formed by wires in a zigzag or meandering form according to an embodiment of the invention.

According to another embodiment of the invention, the metal layer is formed by a surface-roughened thin metal bag with a number of small opening on the circumferential surface of the bag in longitudinal direction.

According to still other embodiment of the invention, the metal layer may be formed by a thin corrugated metal bag.

Preferably it is also provided that the inner surface of said metal jacket is formed with a plastic film having a high resistance to abrasion.

To achieve the above-described second object of the invention, according to another aspect of the invention, there is provided an artificial joint with a metal jacket for the stem of an cementless artificial joint which is integrally formed of a head, neck and stem so as to be inserted into an opening formed by reaming out some part of the bone canal in a human body, wherein the metal jacket is so formed that it may enclose at least a part of said stem and is provided on its outer surface with a surface roughened metal layer so that a mechanical interlocking between the metal jacket and the bone can be made as the bone makes on-growth on the rough surface of the metal layer and wherein the lower end part of the jacket encompasses a surplus space to allow for the stem to slide downward.

In the case of using an artificial joint equipped with a metal jacket for an artificial joint stem according to the invention, predominantly a compressive force takes place between the bone and the metal jacket to suppress the formation of fibrous tissue membrane, to activate or fortify the bone, and to reduce the shear stress detrimental to the bone at the interface between the bone and the metal jacket and turn it into beneficial compressive force. The compressive force acts to minimize the osteolysis of femur due to the infiltration of wear particles by deterring the formation of gap between the bone and the metal jacket.

Further, in the case of using an artificial joint equipped with a metal jacket for a cementless artificial joint stem according to the invention, the vertical force is mostly transferred into the bone hoop stress, which induces a tensile stress large enough to physiologically activate the bone (Wolfe's law) even at the proximal region of the bone, alleviating the phenomena of stress shielding drastically.

Furthermore, the metal jacket for a cementless artificial joint according to the invention has the advantage that while securing physiological interlocking with the bone at normal time, the wire can be easily separated from the plastic film at the time of revision surgery and unwound from the bone due to its inherent characteristic as metal wire, minimizing the damage on the bone.

Further, the generation of wear particles from sliding contact with the stem can be minimized by placing a film of plastic resistant to wearing-out, preferably polyethylene film on the inner surface of the jacket.

Still further, the metal jacket according to the invention has the advantage that direct contact between the bone and the stem is prevented by providing a strong and uniform tube-type layer and breakage of a jacket due to the vertical sinking of a stem is prevented by securing a space between the end of the metal jacket and the end of the stem.

DESCRIPTION OF A PREFERRED EMBODIMENT

A preferred embodiment of a metal jacket for a cementless artificial joint stem and an artificial joint equipped with that metal jacket will be described in detail below by referring to accompanying drawings.

Figure 1:
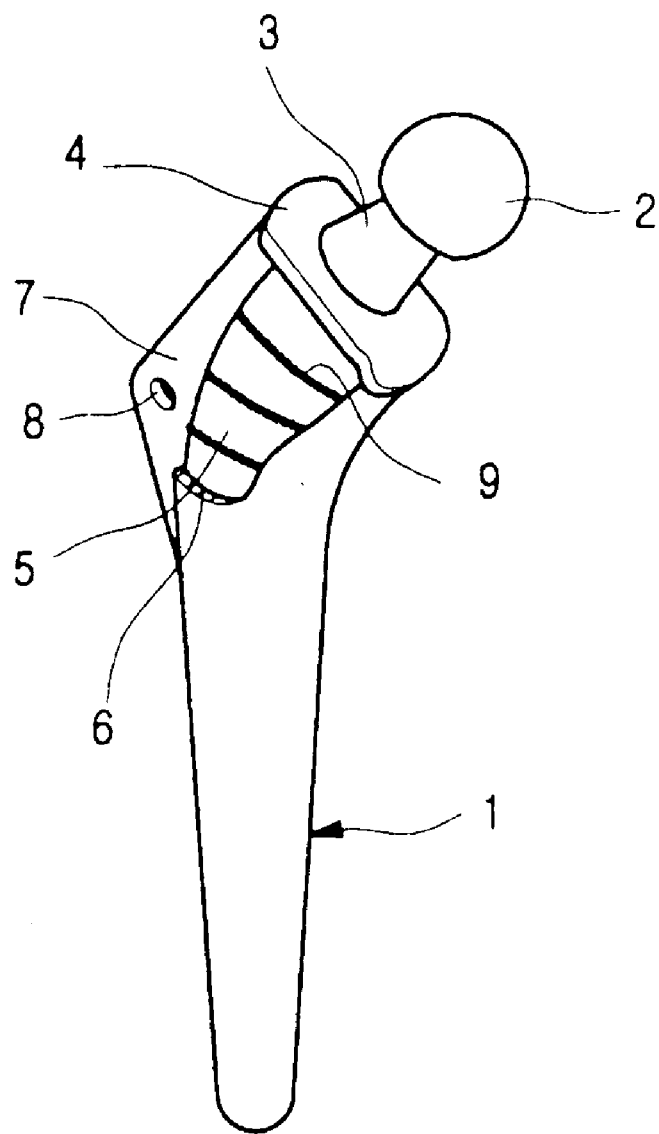
FIG. 1 shows the perspective view of an artificial joint according to a conventional art to illustrate constituting components.
Figure 2:
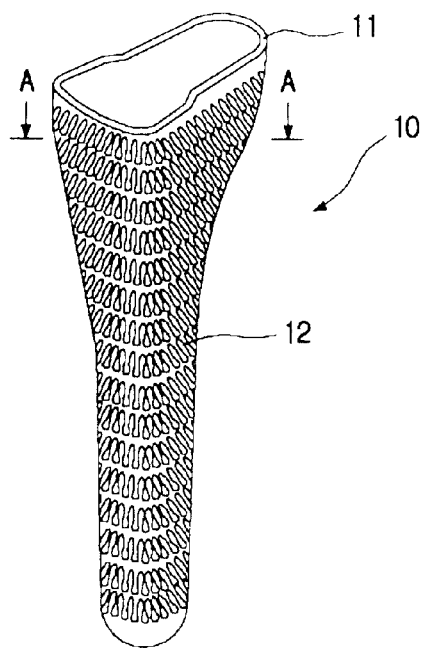
FIG. 2 shows the perspective view of a metal jacket for a cementless artificial joint stem according to an embodiment of the invention to illustrate constituting components.
Figure 3:
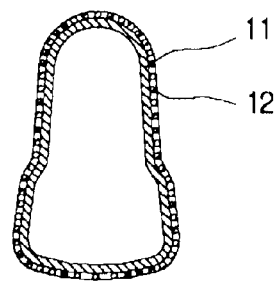
FIG. 3 shows the cross section along the line A—A of the metal jacket for the cementless artificial joint stem shown in FIG. 2.

As can be seen in FIGS. 2 and 3, the metal jacket 10 for a cementless artificial joint stem according to a preferred embodiment of the invention is in the form adapted for enclosing the stem when a stem is inserted, or in the form of a bag. The metal jacket 10 is so formed that the stem may slide down vertically in the jacket when it is inserted and dimensioned in its diameter to match the outer diameter of a stem.

In addition, the metal jacket 10 is formed a little longer than the stem so that a predetermined space between the lower end of the stem and the lower end of the metal jacket remains to prevent the lower tip of the stem from touching the lower end of the metal jacket when the stem is placed in the metal jacket. The formation of such a prescribed space is to prevent a damage on the metal jacket 10, if the stem sinks downward.

Further, the metal jacket 10 is made of plastic layer 11 like an ultrahigh molecular weight polyethylene or equivalent plastic layer to minimize the abrasion owing to the vertical sliding of the stem within the jacket. The surface of the plastic layer 11 is formed additionally with surface-processed metal layer. Such a metal layer is formed of wires 12 of titanium or equivalent metals, the surface of which was roughened by grit blasting, plasma spray or mechanical processing, and which wires wrap the plastic layer 11 zigzag or meanderingly. Wrapping metal wire 12 around the surface of the metal jacket 10 zigzag or meanderingly is intended to transform the vertical force from the head to the compressive stress at the bone canal and to increase the surface area so that interface interlocking can be secured with the on-growth of the bone. Simultaneously the hoop stress can be better transferred to the femur.

The metal layer 12 can be formed, instead of wires, by a surface-roughened thin metal bag with a number of small openings on the surface of the bag, or with a number of folds along the circumference in the longitudinal direction. The reason for forming these openings or folds is to allow radial expansion of the metal bag so that the transference of hoop stress to the femur may be improved.

Now, the procedure of inserting an artificial joint by using the jacket so constructed according to the invention will be described.

Figure 4:
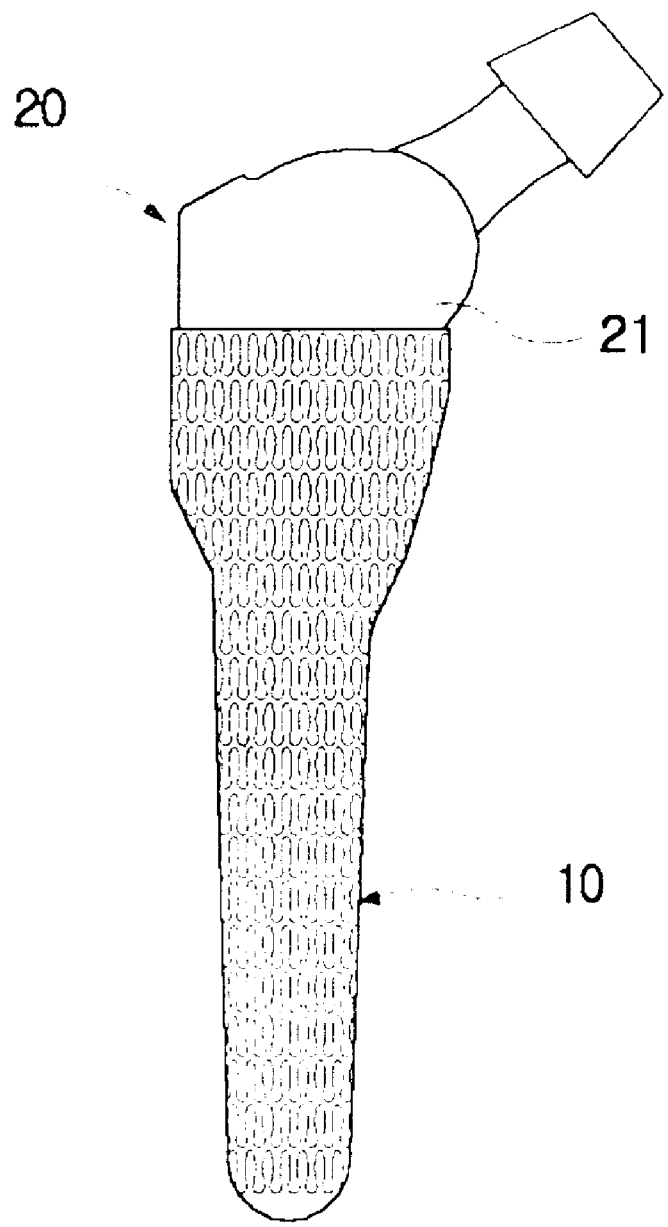
FIG. 4 shows an artificial joint stem as inserted in the metal jacket shown in FIG. 2.

As can be seen from FIG. 4, the stem 21 of a conventional artificial joint 20, the surface of which is polished, is first inserted into a metal jacket 10 according to the invention. Then, a prescribed space between the lower end of a stem 21 and the lower end of a metal jacket 10 is formed, so that the stem 21 can slide down relative to the metal jacket 10, as mentioned earlier.

Figure 5:
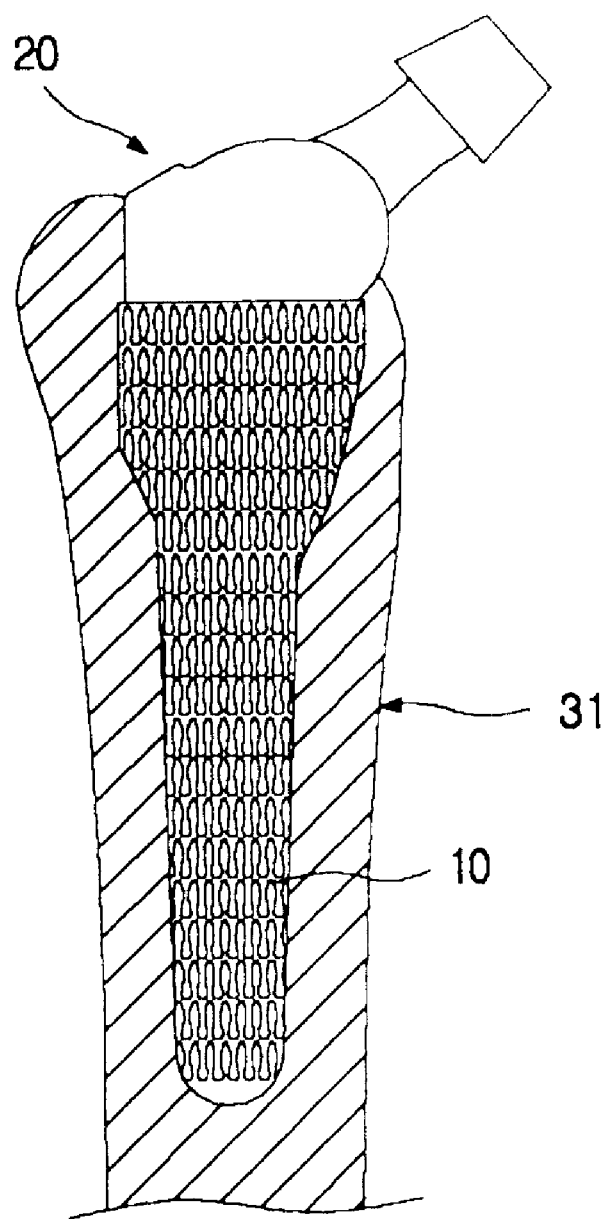
FIG. 5 shows an artificial joint shown in FIG. 4 as inserted in the bone canal in a human body.

Now, the artificial joint 20, wherein the metal jacket 10 is placed over the stem 21, is to be inserted into the bone canal in a human body. To that end, the bone canal is reamed to form an opening, so that a metal jacket 10 in which the stem 21 of artificial joint 20 is placed may be inserted, and thus the artificial joint 20 housed in the metal jacket 10 is inserted there, as seen in FIG. 5. Then, the metal jacket 10 wounded with metal wire 12 gets interlocking physiologically with the bone 31, as the bone 31 makes on-growth on the metal wire. Consequently, the bone 31 and the metal jacket 10 are stoutly combined, while the stem 21 can slide down in relation to the metal jacket 10.

The metal jacket according to the present invention can be applied to all kinds of artificial joint including the hip joint, knee joint, shoulder joint and the like.

It is to be understood that, while the invention was described only with respect to a preferred embodiment of a metal jacket for cementless artificial joint stem and an artificial joint having the same jacket, the invention is never restricted to that embodiment and a variety of modifications and alterations would be possible to a man skilled in the art by referring to the description or drawings presented here and within the spirit of the invention and thus those modifications or alterations are to fall within the scope of the invention, which scope should be limited only by the attached claims.

What is claimed is:

1. A metal jacket for a cementless artificial joint stem, said jacket enclosing at least a part of the cementless artificial joint stem, said stem with jacket being adapted to be inserted longitudinally in the opening formed in the bone canal of a human body, the surface of said jacket having a surface-processed metal layer to thereby interlock the bone in which inserted with the metal layer as the bone gets on-growth onto the metal surface, wherein the inside of said jacket is formed of wear resisting plastics enclosing the metal stem.

2. A metal jacket for a cementless artificial joint stem, said jacket enclosing at least a part of the cementless artificial joint stem, said stem with jacket being adapted to be inserted longitudinally in the opening formed in the bone canal of a human body, the surface of said jacket having a surface-processed metal layer to thereby interlock the bone in which inserted with the metal layer as the bone gets on-growth onto the metal surface, wherein the metal layer is formed by metal wires wound in a zigzag or meandering form, wherein the inside of said jacket is formed of wear resisting plastics enclosing the metal stem.

3. A metal jacket for a cementless artificial joint stem, said jacket enclosing at least a part of the cementless artificial joint stem, said stem with jacket being adapted to be inserted longitudinally in the opening formed in the bone canal of a human body, the surface of said jacket having a surface-processed metal layer to thereby interlock the bone in which inserted with the metal layer as the bone gets on-growth onto the metal surface, wherein the metal layer comprises a surface processed-thin metal bag with a plurality of small openings formed, wherein the inside of said jacket is formed of wear resisting plastics enclosing the metal stem.

4. A metal jacket for a cementless artificial joint stem, said jacket enclosing at least a part of the cementless artificial joint stem, said stem with jacket being adapted to be inserted longitudinally in the opening formed in the bone canal of a human body, the surface of said jacket having a surface-processed metal layer to thereby interlock the bone in while inserted with the metal layer as the bone gets on-growth onto the metal surface, wherein the metal layer comprises of a surface-processed thin metal bag with a plurality of folds formed along the circumference, wherein the inside of said jacket is formed of wear resisting plastics enclosing the metal stem.

* * * * *

UNITED STATES PATENT AND TRADEMARK OFFICE
CERTIFICATE OF CORRECTION

PATENT NO. : 6,497,728 B2
DATED : December 24, 2002
INVENTOR(S) : Yong-San Yoon

It is certified that error appears in the above-identified patent and that said Letters Patent is hereby corrected as shown below:

<u>Title page,</u>
Item [75], Inventors, should read as follows:
-- [75] Inventor: Yong-San Yoon --.

Signed and Sealed this

Seventeenth Day of February, 2004

JON W. DUDAS
*Acting Director of the United States Patent and Trademark Office*